United States Patent [19]

Glenn

[11] 4,317,370

[45] Mar. 2, 1982

[54] ULTRASOUND IMAGING SYSTEM

[75] Inventor: William E. Glenn, Ft. Lauderdale, Fla.

[73] Assignee: New York Institute of Technology, Westbury, N.Y.

[21] Appl. No.: 102,869

[22] Filed: Dec. 12, 1979

Related U.S. Application Data

[63] Continuation-in-part of Ser. No. 806,004, Jun. 13, 1977, abandoned.

[51] Int. Cl.³ ............................................. G01N 29/00
[52] U.S. Cl. ......................................... 73/620; 128/660
[58] Field of Search .................................. 73/620–626, 73/629; 128/660–661; 358/112, 206–208

[56] References Cited

U.S. PATENT DOCUMENTS

| | | | |
|---|---|---|---|
| 3,690,311 | 9/1972 | Schorum et al. | 128/660 |
| 3,798,366 | 3/1974 | Hunt et al. | 128/736 |
| 3,856,985 | 12/1974 | Yokoi et al. | 128/660 |
| 3,864,660 | 9/1974 | Ranalli et al. | 128/660 |
| 3,886,359 | 5/1975 | Cheek, Jr. et al. | 250/334 |
| 3,954,098 | 5/1976 | Dick et al. | 128/661 |
| 4,006,627 | 2/1977 | Bossaert | 73/620 |
| 4,010,466 | 3/1977 | Hofstein | 367/11 |
| 4,032,888 | 6/1977 | Broyles et al. | 358/208 |
| 4,047,520 | 9/1977 | Soldner et al. | 128/660 |
| 4,058,003 | 7/1976 | Macovski | 128/660 X |
| 4,084,582 | 4/1978 | Nigam | 128/660 |
| 4,122,494 | 10/1978 | Levine | 358/208 |
| 4,141,347 | 2/1979 | Green et al. | 128/660 |

FOREIGN PATENT DOCUMENTS

| | | | |
|---|---|---|---|
| 2628567 | 12/1977 | Fed. Rep. of Germany | 367/11 |
| 2710038 | 7/1978 | Fed. Rep. of Germany | 73/620 |
| 67 | 12/1978 | European Pat. Off. | 128/660 |
| 7508732 | 10/1975 | France | 73/620 |
| 7414930 | 11/1975 | France | 73/620 |
| 184000 | 7/1966 | U.S.S.R. | 73/620 |

*Primary Examiner*—Robert W. Michell
*Assistant Examiner*—Francis J. Jaworski
*Attorney, Agent, or Firm*—Martin Novack

[57] ABSTRACT

The disclosure is directed to an apparatus for scanning an object with a beam of ultrasound energy and for formulating image-representative signals from the ultrasound reflected from the object. An ultrasound reflector is disposed in the path of the ultrasound energy, the reflector typically being disposed in a suitable fluid, for example water. The reflector is mechanically driven and means are provided for sensing the relative angular position of the reflector and for generating a first clock signal as a function of the sensed position. Means, responsive to the ultrasound reflected from the object are provided for generating echo-representative electrical signals. These echo-representative electrical signals are stored at a line rate which depends upon the first clock signal. Finally, means are provided for reading out the stored signals at a line rate which depends upon a second clock signal, and for displaying the read out signals to obtain an image of the object, the line rate of the display being synchronized with the second clock rate.

8 Claims, 5 Drawing Figures

ULTRASOUND IMAGING SYSTEM

This is a continuation-in-part of U.S. application Ser. No. 806,004, now abandoned filed June 13, 1977.

BACKGROUND OF THE INVENTION

This invention relates to ultrasonic systems and, more particularly, to apparatus for imaging sections of a body by transmitting ultrasonic energy into the body and determining the characteristics of the ultrasonic energy reflected therefrom.

During the past two decades ultrasonic techniques have become more prevalent in clinical diagnosis. Such techniques have been utilized for some time in the field of obstetrics, neurology and cardiology, and are becoming increasingly important in the visualization of subcutaneous blood vessels including imaging of smaller blood vessels.

Various fundamental factors have given rise to the increased use of ultrasonic techniques. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparant risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedance mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signal representative of detected echoes are amplified and applied to the vertical deflection plates of a cathode ray display. The output of a time-base generator is applied to the horizontal deflection plates. Continuous repetition of the pulse/echo process in synchronism with the time-base signals produces a continuous display, called an "A-scan", in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scanlines on the display, and successive transverse positions are utilized to obtain successive scanlines on the display. This type of technique yields a cross-sectional picture in the plane of the scan, and the resultant display can be viewed directly or recorded photographically or on magnetic tape. The transverse scan of the beam may be achieved by a reflector which is scanned mechanically over a desired angle. It is generally considered desirable that the ultrasound reflector be mechanically scanned at a linear rate which is compatible with a given field rate of a television-type display. Accordingly, an acceptable scan pattern would be controlled by a sawtooth energizing waveform which rises linearly over most of its period and has a relatively short "flyback" (related to vertical blanking of the display), the flyback being as short as possible so that the operational duty cycle is as high as possible.

The described scan of the ultrasound reflector is considered advantageous from the standpoint of compatibility with television-type displays and is intended to provide advantageous linearity during the scan, but it is found that operational difficulties arise. In particular, it is known that ultrasound is highly reflected at liquid-gas interfaces and this has led to the technique of coupling the ultrasound through a fluid. When the reflective scanner is contained in a fluid medium such as water, linear movement and relatively fast flyback can be difficult to attain and/or be mechanically inefficient requiring high input power. This is especially true for equipments wherein relatively large-area scanners, with their attendant inertial resistance to acceleration and deceleration in a fluid, are utilized.

It is one of the objects of this invention to provide an imaging system which is generally responsive to the problems of the prior art, as set forth.

SUMMARY OF THE INVENTION

The present invention is directed to an apparatus for scanning an object with a beam of ultrasound energy and for formulating image-representative signals from the ultrasound reflected from the object. In accordance with the invention, an ultrasound reflector is disposed in the path of the ultrasound energy, the reflector typically being disposed in a suitable fluid, for example water. The reflector is mechanically driven and means are provided for sensing the relative angular position of the reflector and for generating a first clock signal as a function of the sensed position. Means, responsive to the ultrasound reflected from the object, are provided for generating echo-representative electrical signals. These echo-representative electrical signals are stored at a line rate which depends upon the first clock signal. Finally, means are provided for reading out the stored signals at a line rate which depends upon a second clock signal, and for displaying the read out signals to obtain an image of the object, the line rate of the display being synchronized with the second clock rate.

In the preferred embodiment of the invention, the means for driving the reflector is adapted to drive the reflector at a non-linear rate, for example, sinusoidally. This is advantageous in that the drive can be applied at a frequency which approximates a resonance of the reflector in the fluid, and the abrupt motions of a sawtooth drive are avoided. In thus embodiment, the duty cycle of the scan is enhanced by storing and displaying information obtained during both the positive and negative-going cycles of the sinusoidal drive. In other words, information is obtained and displayed while scanning in both directions, so there is no wasted flyback period. In the preferred embodiment, the electrical signals are stored in shift registers. The information stored during an angular sweep of the scanner in one direction is read out on a "first-in-first-out" basis, whereas the information stored during the sweep of the scanner in the opposite direction is read out on a "last-in-first-out" basis.

In an embodiment of the invention, the means for sensing the position of the reflector comprises a shaft encoder and the shift registers used for storage are analogue registers of the charge transfer type.

Further features and advantages of the invention will become more readily apparent from the following detailed description when taken in conjunction with the accompanying drawings.

DESCRIPTION OF THE PREFERRED EMBODIMENT

Figure 1:
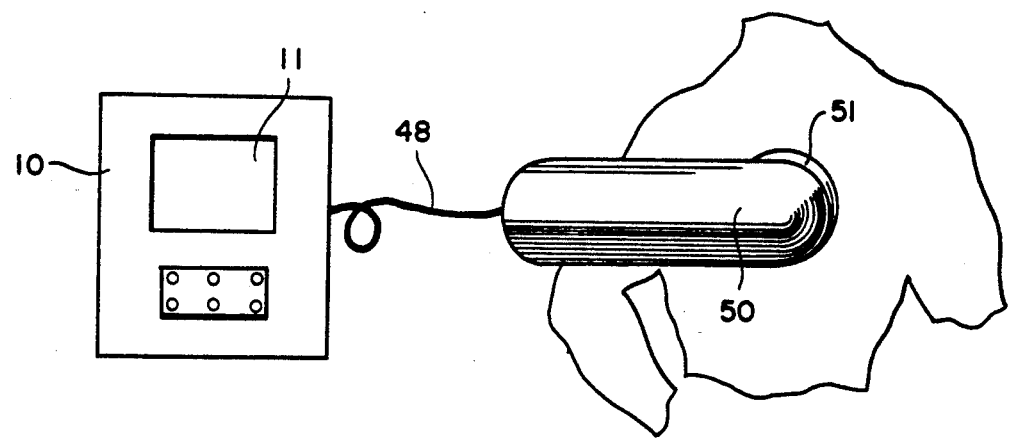
FIG. 1 illustrates the operation of a scanning apparatus which employs the improvements of the invention.

Referring to FIG. 1, there is shown an illustration of a scanning apparatus which employs the improvements of the invention. A console 10 is provided with a display 11 which may typically be a cathode ray tube television-type display, and a suitable control panel. A video tape recorder or suitable photographic means may also be included in the console to effect ultimate display of images. The console will typically house power supplies and portions of the timing and processing circuitry of the system to be described. A portable scanning module or probe 50 is coupled to the console by a cable 48. In the present embodiment the probe is generally cylindrical in shape and has a scanning window 51 near one end, the scanning window being defined by protruding flexible material, which may typically be silicone rubber. During operation of the apparatus, the probe 50 is handheld to position the scanning window over a part of the body to be imaged. For example, in FIG. 1 the probe is positioned such that a cross section of the heart will be obtained. Imaging of other portions of the body is readily attained by moving the probe to the desired position and orientation, the relative orientation of the scanning window determining the angle of the cross section taken.

Figure 2:
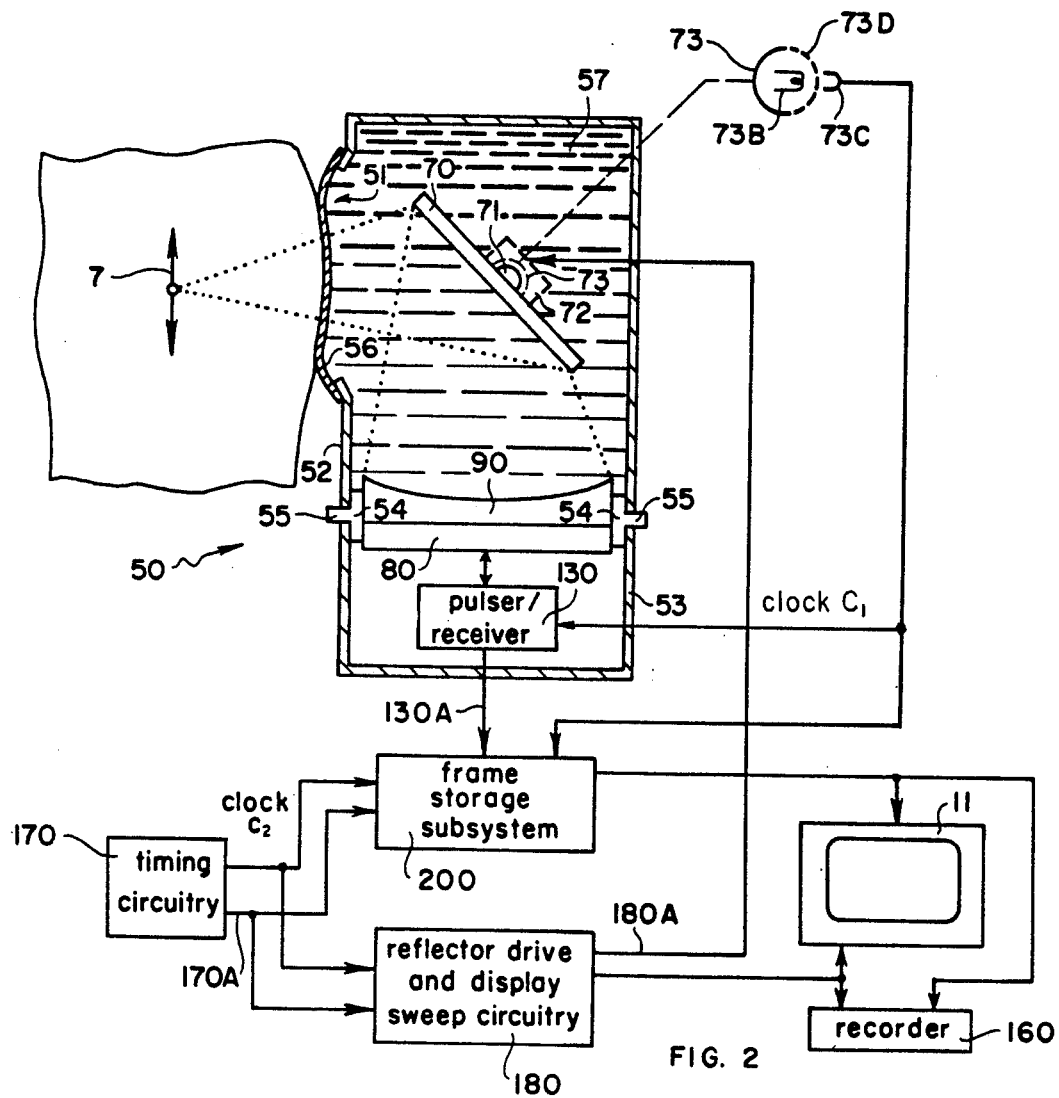
FIG. 2 is a schematic diagram, partially in block form, of an apparatus in accordance with the embodiment of the invention.

Referring to FIG. 2, there is shown a cross-sectional view of a portion of the scanning module or probe 50 along with diagrams of portions of the circuitry therein and in console 10 used in conjunction therewith. An enclosure, which may be formed of plastic, consists of a front cover 52 which defines a fluid-tight compartment, and a rear cover 53 which houses at least a portion of the system electronics. Both covers are generally cylindrical in shape and fit, with suitable seals, over a cylindrical inner housing 54 having an annular rim 55. The inner housing holds a transducer 80 and a focusing lens 90, which may be in accordance with the description set forth in the U.S. Pat. No. 3,958,559. The scanning window 51 is defined by a generally rectangular opening in the side of cover 52, the opening having a slightly protruding lip on which is mounted a flexible material 56, which may be a silicone rubber membrane. The volume of the enclosure defined by front cover 52 is filled with a fluid 57, for example, water. The membrane 56 will accordingly conform in shape to the surface of a body portion with which it is placed in contact, thereby minimizing the possibility of an undesirable reflective liquid-air interface.

A reflective scanner 70, which is flat in the present embodiment but which may be curved to provide focusing if desired, is disposed in the fluid 57 between the lens 90 and the scanning window 51. The scanner 70 is mounted on a shaft 71 (perpendicular to the plane of the paper) which passes through a suitable seal in cover 52 and is connected to a small electric motor 72 which is mounted on the outside of cover 52 and provides the desired oscillatory motion. A shaft encoder unit 73, which is shown schematically in the insert in FIG. 2, is mounted partially on the shaft and partially on the cover 52. The motor and shaft encoder, which are shown in dashed line in the FIGURE, may be provided with a small separate cover (not shown) which constitutes a protrusion on the cover 52, or an irregular outer shape can be avoided by providing a secondary larger outer shell (not shown).

The transducer 80 is coupled to a pulser/receiver circuit 130 which alternately provides energizing pulses to and receives echo signals from the transducer 80. If desired, coupling between the pulser/receiver 130 and the transducer 80 may be via variable delay circuitry (not shown) which includes variable delay elements and provides dynamic focusing of the ultrasound beam, in a manner well known in the art. Dynamic focusing circuitry is generally employed in conjunction with a segmented transducer and, if desired, a stepped focusing lens, as disclosed in the copending U.S. application Ser. No. 665,898, now U.S. Pat. No. 4,084,582, assigned to the same assignee as the present application. The receiver portion of circuit 130 includes a preamplifier and is coupled to a frame storage subsystem 200 (via line 130A). The output of the frame storage subsystem 200 is coupled to display 11 and recorder 160, which may be any suitable recording or memory means such as a video tape recorder. If desired, gain control circuitry may be provided and may include interactive gain compensation, which is described in detail in U.S. Pat. No. 4,043,181, assigned to the same assignee as the present application. Interactive gain compensation circuitry compensates the amplitude of later arriving signals for attenuation experienced during passage through body tissue and losses due to prior reflections. Timing circuitry 170 generates timing signals which synchronize operation of the system; the timing signals being coupled to the circuitry 200 and also to reflector drive and display sweep circuitry 180 which generates the signals that control the oscillation of scanner 70 and the vertical and horizontal sweep signals for the display 11 and recorder 160.

In broad terms, operation of the system is as follows: The pulser in circuitry 130 generates pulses which excite the transducer 80. The resultant ultrasound energy is focused by the lens 90 and reflected off the surface of scanner 70 and into the body 5, as represented in FIG. 2, the dashed line depicting the beam outline. When the beam has been transmitted toward the body, the timing circuitry causes the pulser/receiver 130 to switch into a "receive" or "listen" mode. Now, the transducer 80 serves to convert ultrasound energy, which is in the form of echoes reflected from the body and back off the scanner 70, into electrical signals. These signals are coupled, via the frame store unit 200, to the display 11. For a "B-scan" display, a sweep over a range of depths (which naturally results from the transmitted energy reflecting off different interfaces in the body) corresponds to a horizontal scanline of the display. The second dimension of the desired cross-sectional image is obtained by a slower mechanical scan of scanner 70, the mechanical scanning range being illustrated by the double-headed arrow 7.

Description in further detail will now be set forth. Clock signals $C_1$ obtained from the shaft encoder control the pulser/receiver 130 to produce pulses at the rate of one for each scanline of the video signal to be ultimately displayed on the display 11. As is well known in the art, each scanline in a B-scan system represents echo information, with the later arriving echoes representing successively deeper investigation into the body. The timing circuitry 170 generates clock signals and timing signals, to be described, which are coupled to reflector drive and display sweep circuitry 180 and the frame storage subsystem 200. One of the timing inputs to the circuitry 180 and subsystem 200 is a clock signal $C_2$, which is at a frequency that determines the line rate of the display 11. The remaining timing signals are represented in general in FIG. 2 by a separate cable designated 170A.

The reflector drive and display sweep circuitry 180 generates vertical and horizontal sweep signals that are coupled to the display 11 and recorder 160 and also generates a motor drive signal, on a line 180A, which is coupled to the motor 72 which provides the desired oscillatory motion of the scanning reflector 70. In the present embodiment, the reflector drive signal is nonlinear, preferably sinusoidal, rather than the usual sawtooth drive waveform (which would typically be similar to the shape of the waveform of the horizontal sweep signal for display 11). The output of shaft encoder 73 is a clock signal, designated as clock $C_1$ which consists of a train of pulses that represent incremental angular displacements of the reflector 70. This may be achieved, for example, and as shown in FIG. 2, by providing a stationary light source 73B and photodetector 73C which are separated by an apertured ring 73D that has equally spaced apertures thereon and is mounted to move with the motor shaft. Unlike the clock pulses $C_2$, which are periodic at the line rate, the clock pulses $C_1$ will have relative time spacings that are irregular and which relate to the scan velocity of scanner 70 during different portions of its scan. In the present embodiment, the scanner is driven sinusoidally, and the clock pulses $C_1$ will be closest together during the center of the scan when the reflector is moving fastest and will be relatively farther apart when the reflector is at the extremes of its oscillatory scan and slows down to change direction. This is shown, for example, in FIG. 5E which is described further hereinbelow. In the present embodiment, the clock pulses $C_1$, which are substantially synchronized in time with the position of reflector 70 and thus the transverse position of the ultrasound beam, are utilized to clock lines of echo-representative information into the frame storage subsystem 200, which preferably comprises a charge transfer type of register such as a charge couple device ("CCD") frame store. The information is subsequently clocked out using the periodic clock $C_2$ to clock out lines of information in synchronization with scanlines of the display 11. In this manner, the scanner 70 can be driven in an efficient non-linear manner, for example near a natural resonance, and accurate imaging information can still be displayed using conventional display equipment.

Figure 3:
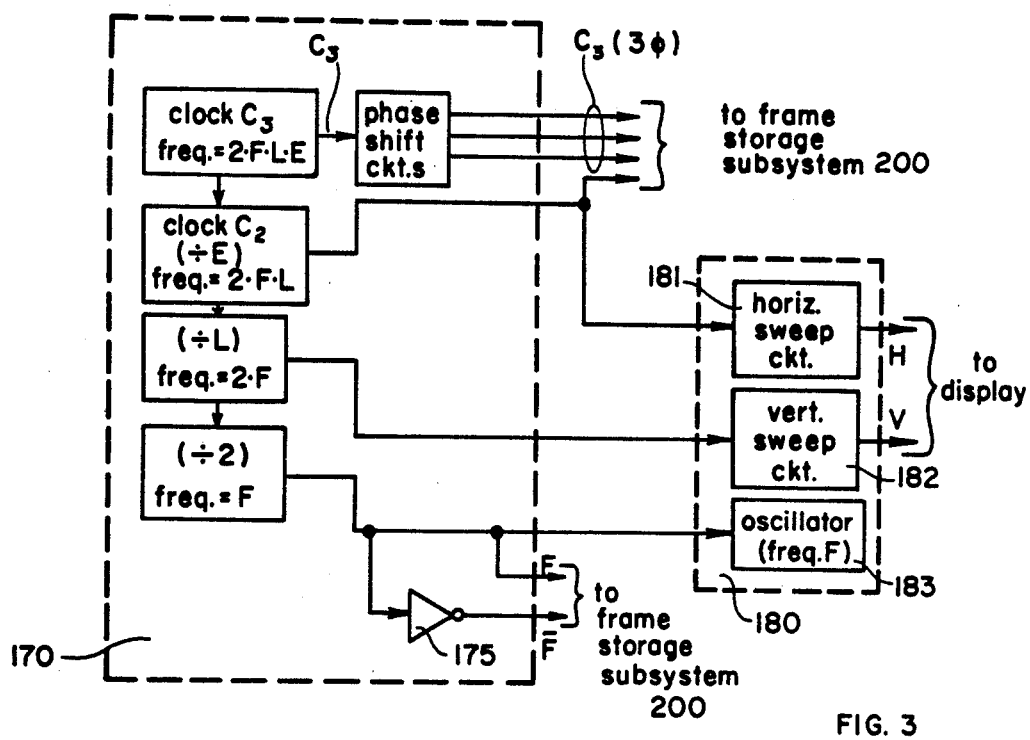
FIG. 3 is a block diagram of the timing circuitry and the reflector drive and display sweep circuitry of FIG. 2.

Referring to FIG. 3, there is shown in further detail the timing circuitry 170 and reflector drive and display sweep circuitry 180 utilized in an embodiment of the invention wherein imaging information is obtained during excursions of the scanner 70 in both directions. In this embodiment, the effective duty cycle of the equipment is enhanced since there is no wasted flyback period, and a smooth sinusoidal drive of the reflector can be employed. Briefly, this is achieved by utilizing a pair of field stores in the frame storage subsystem 200 (FIG. 2), these field stores being described in further detail in conjunction with FIG. 4. When one of the field stores is having new information clocked into it (during an excursion of the reflector 70 in one direction), the other field store is having previously stored information clocked out of it for display on the display 11. During the subsequent excursion of the reflector in the opposite direction, the reverse situation is effective, so that the field stores alternately store and read out information to the display. In FIG. 3, F represents the frame rate at which the display 11 is to operate (2F being the field rate), L represents the number of lines at which the display is to operate, and E represents the number of elements per scanline. Since F will also correspond to the frequency of oscillation of the reflector 70, it can be selected to be at or near the natural resonant frequency of the scanner in its fluid environment. Typically, F may be 15 Hz. and L and E selected using considerations of resolution and bandwidth. For example, one might select 250 lines per field for an interlaced 500 lines per field, and 500 elements per line, so that L would be 250 and E would be 500.

The basic high frequency clock for the system is the clock $C_3$ which produces clock pulses at a frequency of $2 \cdot F \cdot L \cdot E$. As will be described, the clock $C_3$ determines the basic sampling rate at which samples are stored by the frame storage subsystem 200. Phase shift circuitry 171 produces three phases of the clock $C_3$, at relative phases of 120° with respect to each other. A clock $C_2$ generates clock pulses at the line rate ($2 \cdot F \cdot L$), this being achieved by dividing the frequency of the clock $C_3$ by E. A clock designated 2F obtains clock pulses at the rate 2F by dividing the frequency of clock $C_2$ by L to produce clock pulses at the field rate. Another clock, designated F, divides the field rate clock by two to obtain pulses at the frame rate, F.

As previously noted, the clock $C_2$, which operates at the nominal line rate, is utilized for clocking line information out of the frame storage subsystem 200, and is also utilized to synchronize the horizontal scanlines of display 11. The last-mentioned function is indicated by the coupling to horizontal sweep circuitry 181 which is part of the reflector drive and display sweep circuitry 180. The clock pulses at the field rate 2F are utilized to synchronize the field rate of the display, as is indicated by the coupling to vertical sweep circuitry 182 in the reflector drive and display sweep circuitry 180. The outputs of circuits 181 and 182, which may be conventional sweep generators, are the horizontal and vertical sweep signals which are typically coupled to the deflection coils of the display 11. The clock which operates at the frame rate F is utilized to synchronize an oscillator 183 that generates a sinusoidal drive at the frequency F (as shown in FIG. 5A) for energizing the reflector motor 72. The clock pulses at the frame rate F are additionally coupled to an inverter 175 so that clock pulses designated $\overline{F}$ are also available at the frame storage subsystem 200, the clock $\overline{F}$ being of opposite phase from the clock F.

Figure 4:
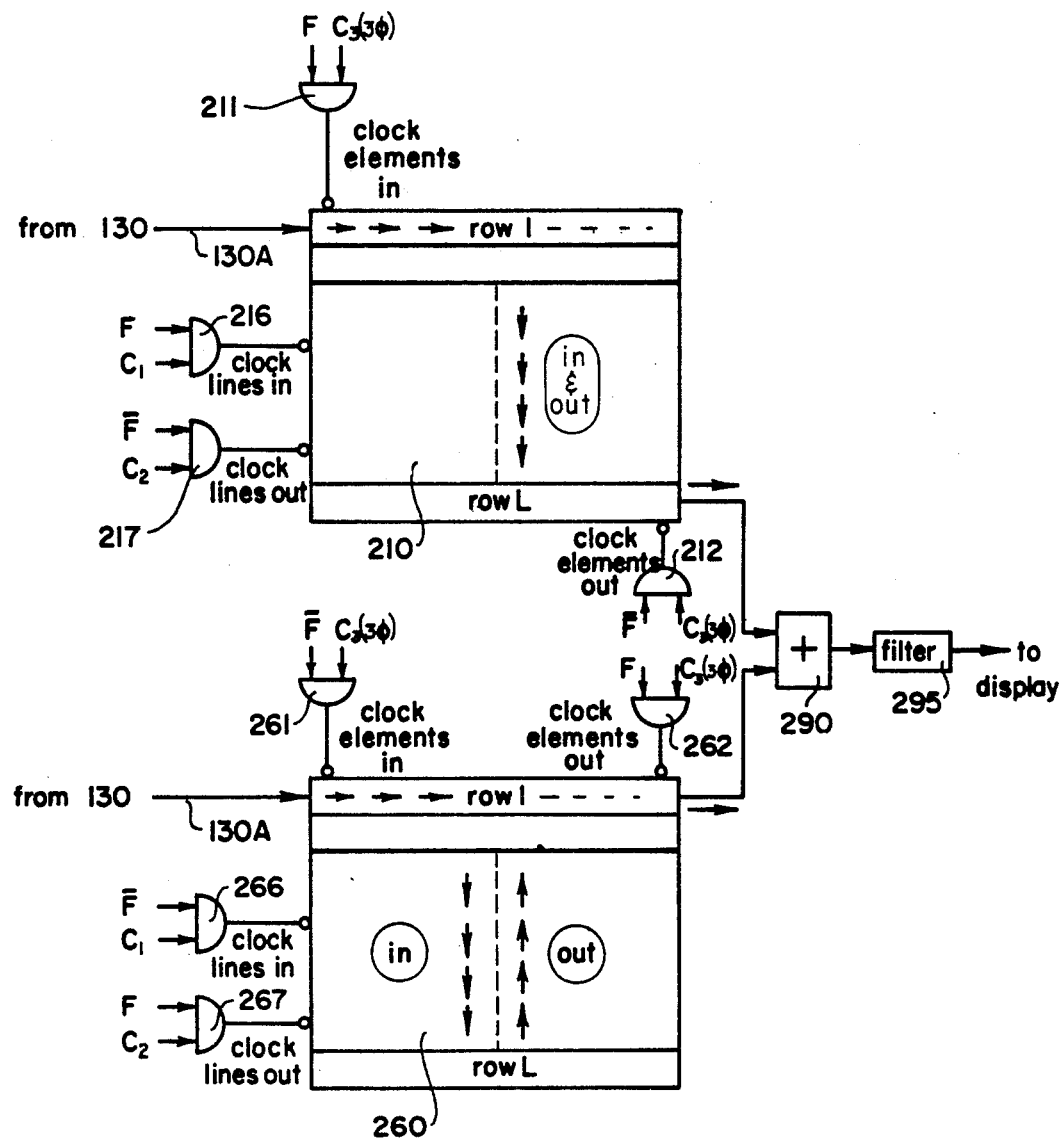
FIG. 4 is a block diagram of an embodiment of the frame storage subsystem of FIG. 2.

Referring to FIG. 4, there is shown an embodiment of the frame storage subsystem 200 of FIG. 2. A pair of field store registers 210 and 260 are provided. These field stores are preferably of the analog charge transfer type, such as three-phase charge coupled device (CCD) field stores. Field stores of the general type described are known in the art and reference is made, for example, to the field storage techniques disclosed in U.S. Pat. No. 3,882,271. The referenced patent describes the manner in which a video-representative signal can be sampled and stored in a frame storage register by sampling information on each line to read a full line of information into the field store, and then shifting the full line of information to the next row of the field store whereupon the next line of information is sampled and read in. It will be understood, however, that various types and arrangements of field stores, including field stores which are commercially available, can be utilized in conjunction with the present invention.

To illustrate operation of the field store 210, a line of information is clocked into a row of CCD elements designated row 1, under control of the three phases of the clock $C_3$, in a manner well known in the art. At the end of the line, the line of information in row 1 is clocked (in parallel) into row 2, this being done by the clock $C_1$ which is obtained from the shaft encoder (FIG. 2). The next line of information is then clocked in at the sample rate, $C_3$, and all previously stored lines of information are then clocked in parallel to the next row using the clock $C_1$. This continues until a full field of information has been clocked into the field store 210 and the first scanline of the field is in the last row (row L), the second scanline of the field is in the next to last row (row L-1) . . . and the last scanline of information is in the first row. Information is subsequently clocked out of the field store 210 on a first-in-first-out basis. In particular, elemental samples are again clocked out using the clock $C_3$, but now the lines of information are clocked from row to row using the periodic clock $C_2$, which operates at the line rate, as previously described. Information is clocked out of row L as indicated by the arrow. When a full line of information has been clocked out using the sample clock $C_3$, the lines of information are clocked in parallel to the next row using the clock $C_2$, and the second line of information is then clocked out using clock $C_3$, and so on. This continues until the entire field of information has been clocked out. The clocked out information is coupled via adder 290 which combines the signals from the two field store units, and via filter 295 which removes the clock frequencies from the signal, to the display 11.

Operation of the field store 260 is similar to that of the field store 210 except that the field store 260 clocks information in and out in a phase which is opposite to that of field store 210. Also, the field store 260 is operative to clock lines of information out on a last-in-first-out basis. In other words, lines are clocked into the rows of field store 260 in the same manner described with respect to field store 210, but during the clocking out of lines the information in the various rows is shifted in the opposite direction from the direction during clocking in, such that elemental samples are clocked out from the end of row 1 (rather than from the end of row L as is the case for field store 210).

Overall operation of the frame storage subsystem 200 is as follows: During scanning by the reflector 70 in one direction, lines of echo-representative information are clocked into the "odd" field store 210 in the manner described. During scanning of the reflector in the opposite direction, the information in "odd" field store is clocked out for display and the new echo-representative information is clocked into the "even" field store 260. Subsequently, while the information now stored in field store 260 is being clocked out for display, new information is being clocked into field store 210, and so on. Since the information from the two fields is combined to form a single frame, and the beam is scanning in opposite directions the two fields, the fields are properly correlated by reading out the lines of field store 210 on a first-in-first-out basis and the lines of field store 260 on a last-in-first-out basis. It should be noted that while the line information during the two fields is clocked out in opposite senses, the sample information for each line may always be clocked out on a last-in-first-out basis.

Before referring to further circuits details of FIG. 4, it should be understood that the convention utilized in the present embodiment is as follows: Recall that the two oppositely phased frame rate clocks are designated F and $\overline{F}$. During each frame half-cycle (field) when F is positive, the "odd" field store 210 shall be clocking information in and the "even" field store 260 shall be clocking information out. Conversely, when the clock signal $\overline{F}$ is positive, the field store 260 shall be clocking information in and the field store 210 shall be clocking information out.

Clocking in of samples to the field store 210 is under control of AND gate 211 which couples the three-phase clock $C_3$ to the field store 210 when enabled by positive cycles of the clock F. For clocking out of the elemental samples of each scanline, another AND gate 212 enables the three phase clock $C_3$ during the positive portions of the clock signal $\overline{F}$. The clocking into and out of the field store 260 is opposite in phase from the description of field store 210. In particular, the AND gate 261, which controls clocking in, is enabled by the positive portions of the clock signal $\overline{F}$ and the clocking out is controlled by the AND gate 262 which is enabled by the positive portions of the clock signal F. The line clocking is achieved, with respect to field store 210, by the clocking in of line information with clock $C_1$ via AND gate 216, and then clocking out of line information using the clock $C_2$ via the AND gate 217. The AND gate 216 is enabled by the positive portions of the clock signal F, and the AND gate 217 is enabled by the positive portions of the clock signal $\overline{F}$. Accordingly, and consistent with the above-listed convention, clocking in with the clock $C_1$ is performed every other field and clocking out using the clock $C_2$ is performed during the intervening fields. The opposite is true in the case of the field store 260 wherein the AND gate 266, which receives the clock $C_1$ as one input, is enabled by the positive portions of clock $\overline{F}$, and the AND gate 267, which receives the clock $C_2$ as one input, is enabled by the positive portions of the clock signal F. In the case of field store 260, the row-to-row connections for shifting line information in the field store are in reverse relationship for clocking in and clocking out, this being done so that the packets of charge are "moved" in opposite directions every other field cycle, to achieve last-in-first-out operation for the lines of information.

Figure 5:
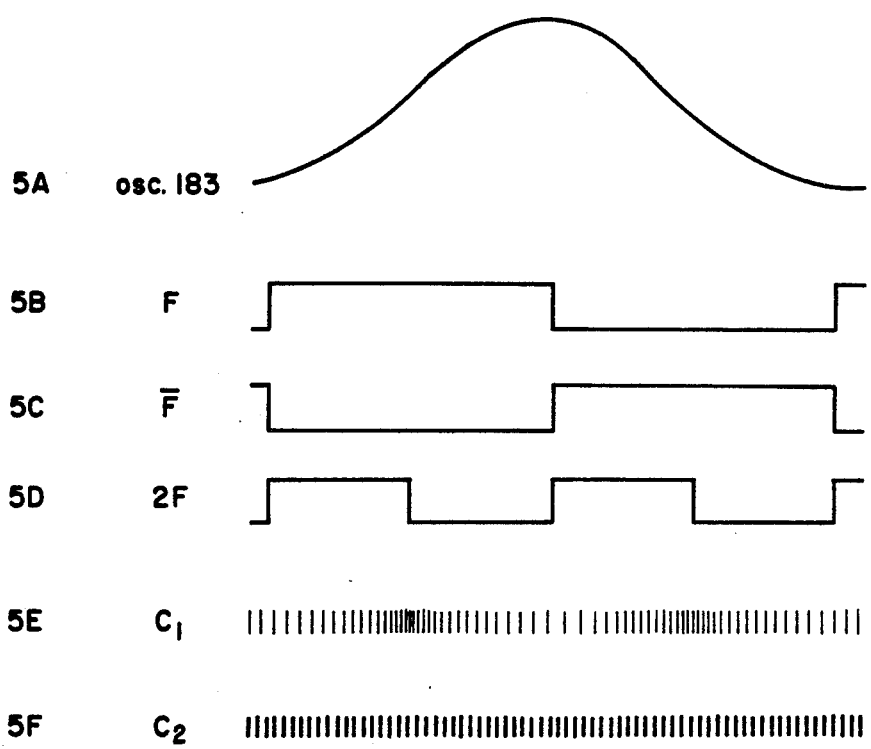
FIG. 5, consisting of FIGS. 5A–5F, shows timing diagrams which are useful in understanding operation of an embodiment of the invention.

To better understand operation of the invention, reference is made to the timing diagrams of FIG. 5 which depict various signals in the present embodiment. FIG. 5A shows the sinusoidal drive which is output of the oscillator 183 and operative to drive the reflector 70 in oscillatory motion. The frequency of the sinusoid corresponds to the frame rate, F. During the rise of the signal, the reflector 70 is scanned from left to right, causing the beam to also scan from left to right. During the fall time of the sinusoid, the reflector 70 is caused to scan back from right to left (the portion of the scan that is generally used for "flyback"). FIGS. 5B and 5C show the frame rate clock signals F and $\overline{F}$ and FIG. 5D shows the field rate clock 2F from which the vertical sweep signal V for the display is derived by sweep circuit 182 (FIG. 3). FIG. 5E illustrates the nature of the clock signal $C_1$ derived from the shaft encoder 73 and FIG. 5F depicts the nature of the clock signal $C_2$ generated as shown in FIG. 3. In FIGS. 5E and 5F the vertical lines represent clock pulses and the actual number of such pulses is not intended to represent the actual number of lines during each field, which would typically be larger than that shown. It is seen that in the case of the clock $C_1$, which is derived from the shaft encoder, the pulses are further apart at those positions near where the reflector is about to change direction or has just changed direction (i.e., near where the sinusoid has a slope close to zero) and are closer together when the reflector is travelling at maximum speed near the center of each excursion from right to left or left to right (i.e., where the sinusoid has maximum slope). This pattern results from obtaining the clock $C_1$ as a function of the relative angular position of the reflector 70. The clock $C_2$ is periodic and is generated at the display line rate by the divider of FIG. 3. During the first half cycle of the frame rate clock, F, the clock pulses $C_1$ are used to clock lines of information into the field store 210 (by operation of gate 216 which is enabled by F) and the clock $C_2$ is used to clock lines of information out of field store 260 (by operation of gate 267 which is also enabled by F). During the next half cycle of the frame rate clock (during which $\overline{F}$ is positive), the clock $C_1$ is utilized to clock the lines of the next field of information into the field store 260 (by virtue of gate 266 being enabled by $\overline{F}$) and the clock $C_2$ is utilized to clock lines of information out of the field store 210 (by virtue of gate 217 being enabled by $\overline{F}$). Accordingly, it is seen that the scanner 70 can be driven in an advantageous manner from the standpoint of mechanical dynamics, and that the duty cycle of operation is enhanced. The number of apertures in the apertured wheel 73D of shaft encoder 73 should preferably be set equal to L so that the number of clock pulses $C_1$ during a field equals the number of clock pulses $C_2$.

I claim:

1. Apparatus for scanning an object with a beam of ultrasound energy and for formulating an image from the ultrasound reflected from the object, comprising:
    an ultrasound reflector disposed in the path of said ultrasound energy;
    a fluid surrounding said reflector;
    means for mechanically driving said reflector in an oscillatory fashion at a non-linear rate;
    means for sensing the relative angular position of said reflector;
    means for generating a first continuously variable clock signal as a function of the sensed position;
    means responsive to the ultrasound reflected from said object for generating echo-representative electrical signals;
    means for storing said electrical signals at a line rate which depends upon said first clock signal;
    means for generating a second periodic clock signal;
    means for reading out the stored signals at a line rate which depends upon said second clock signal; and
    means for displaying the read out signals to obtain an image of the object, the line rate of said display being synchronized with said second clock signal.

2. Apparatus as defined by claim 1 wherein said means for driving the reflector is adapted to drive the reflector substantially sinusoidally.

3. Apparatus as defined by claim 1 wherein said means for sensing the position of said reflector comprises a shaft encoder.

4. Apparatus as defined by claim 1 wherein said means for storing the echo-representative electrical signals comprises a charge transfer register.

5. Apparatus as defined by claim 1 wherein said means for storing the echo-representative electrical signals comprises a pair of charge transfer registers.

6. Apparatus as defined by claim 5 further comprising means for effecting storage of said echo-representative electrical signals in one of said charge transfer registers during one half-cycle of a reflector drive period and for effecting storage of said echo-representative electrical signals in the other of said charge transfer registers during the other half-cycle of a reflector drive period.

7. Apparatus as defined by claim 6 wherein said means for effecting storage of said echo-representative signals is also operative to effect the reading out of lines of said stored signals at said second clock rate from each of said charge transfer registers during the time that the other charge transfer register is storing the echo-representative electrical signals at said first clock rate.

8. Apparatus as defined by claim 7 wherein one of said charge transfer registers is a field store operative to read out lines of information on a first-in-first-out basis and the other of said charge transfer registers is a field store operative to read out lines of information on a last-in-first-out basis.

* * * * *